United States Patent
Dhawan et al.

(10) Patent No.: US 8,163,961 B2
(45) Date of Patent: *Apr. 24, 2012

(54) PROCESS FOR THE PREPARATION OF MONOMERS FOR POLYBENZIMIDAZOLE MATERIALS

(75) Inventors: Rajiv Dhawan, Wilmington, DE (US); Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,799

(22) Filed: Feb. 22, 2010

(65) Prior Publication Data

US 2010/0160676 A1 Jun. 24, 2010

Related U.S. Application Data

(60) Provisional application No. 61/138,678, filed on Dec. 18, 2008.

(51) Int. Cl.
*C07C 211/00* (2006.01)

(52) U.S. Cl. ........ 564/441; 564/305; 564/306; 564/415; 564/416; 562/480

(58) Field of Classification Search ............... None
See application file for complete search history.

(56) References Cited

U.S. PATENT DOCUMENTS

| | | | | |
|---|---|---|---|---|
| 3,174,947 A | * | 3/1965 | Marvel et al. | 528/331 |
| 3,476,590 A | | 11/1969 | Rabilloud et al. | |
| 3,783,137 A | * | 1/1974 | Gerber et al. | 528/208 |
| 4,533,692 A | * | 8/1985 | Wolfe et al. | 524/417 |
| 5,041,522 A | * | 8/1991 | Dang et al. | 528/183 |
| 6,040,478 A | | 3/2000 | Sikkema et al. | |

FOREIGN PATENT DOCUMENTS

| | | |
|---|---|---|
| EP | 237955 | 7/1992 |
| JP | 2005-330470 | 12/2005 |

OTHER PUBLICATIONS

Ritter et al., U.S. Appl. No. 61/138,602, filed Dec. 18, 2008.
Ritter et al., U.S. Appl. No. 61/138,615, filed Dec. 18, 2008.
Dhawan et al., U.S. Appl. No. 61/138,626, filed Dec. 18, 2008.
Ritter. U.S. Appl. No. 61/138,672, filed Dec. 18, 2008.
Dhawan et al., U.S. Appl. No. 61/138,696, filed Dec. 18, 2008.
Dhawan et al., U.S. Appl. No. 61/138,662, filed Dec. 18, 2008.
Cotton and Wilkinson, Advanced Inorganic Chemistry, Periodic Table Only, 1966, Interscience Publishers, $2^{nd}$ Edition, New York.

* cited by examiner

*Primary Examiner* — Sudhakar Katakam

(57) ABSTRACT

Complexes of 2,3,5,6-tetraaminotoluene with an aromatic diacid are prepared by reaction with a divalent salt of the aromatic diacid while maintaining the pH of the reaction solution between 3 and 10. The resulting complexes are suitable for making high molecular weight polybenzimidazole polymers for high-performance fibers.

6 Claims, 1 Drawing Sheet

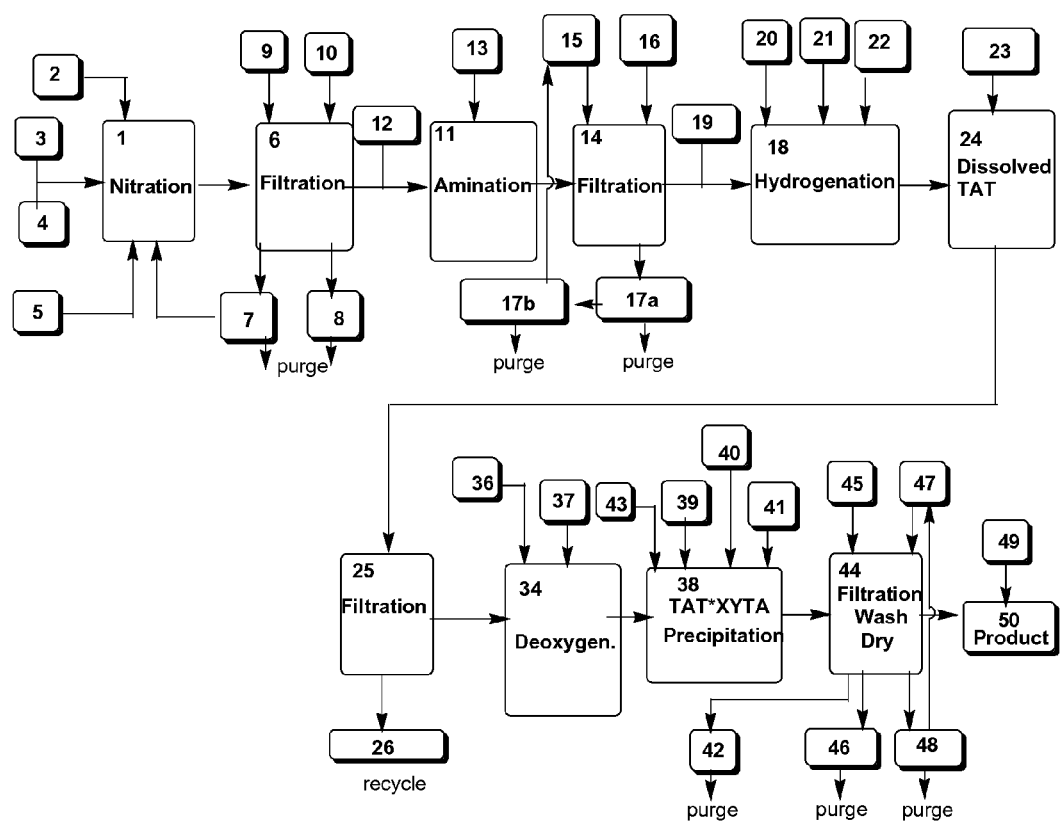

PROCESS FOR THE PREPARATION OF MONOMERS FOR POLYBENZIMIDAZOLE MATERIALS

This application claims priority under 35 U.S.C. §119(e) from, and claims the benefit of, U.S. Provisional Application No. 61/138,678, filed Dec. 18, 2008, which is by this reference incorporated in its entirety as a part hereof for all purposes.

TECHNICAL FIELD

This disclosure relates to methods of making complexes of 2,3,5,6-tetraaminotoluene with aromatic diacids, which are then used to make high-performance polybenzimidazole polymers.

BACKGROUND

The synthesis of preferred polybenzimidazole based high performance fibers requires the selective polymerization of 2,3,5,6-tetraaminotoluene ("TAT") with various substituted and unsubstituted aromatic diacids, such as 2,5-dihydroxyterephthalic acid ("DHTA"). This requires the synthesis and subsequent condensation polymerization of a 1:1 complex between the diacid and the tetraamine. The ratio of diacid to tetraamine must be as close to 1:1 as possible to achieve high molecular weight. A critical polymer property is intrinsic viscosity. Only material with sufficiently high intrinsic viscosity (i.e., high molecular weight) is suitable for the production of a high tensile strength fiber.

A commercially viable process producing the monomers of fiber-grade purity and in a form allowing for the production of high molecular weight polymer requires a high space time yield process for the synthesis of a 1:1 complex between diacid and tetraamine. A need thus remains for a process for the production of a suitable TAT-diacid monomer complex that can be polymerized to a high molecular weight polymer material for producing high-performance fibers, wherein the complex is formed from a stable precursor without isolation of intermediates.

SUMMARY

In one embodiment, this invention provides a process for preparing a complex generally described by Formula I

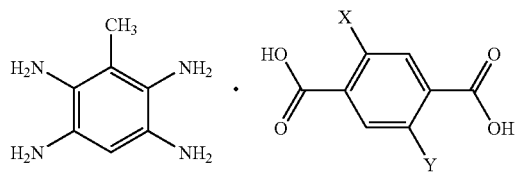

I wherein X and Y are each independently selected from the group consisting of H, OH, SH, methyl, ethyl, F, Cl, and Br; comprising the sequential steps under exclusion of oxygen:
  a. contacting 2,3,5,6-tetraaminotoluene (Formula II)

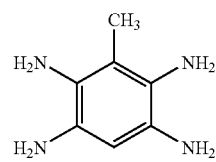

II with an aqueous solution comprising 1 to 6 equivalents of acid per mol of 2,3,5,6-tetraaminotoluene, optionally heating the solution, thereby dissolving the 2,3,5,6-tetraaminotoluene;
  b. combining the dissolved 2,3,5,6-tetraaminotoluene with
    i. 0 to 5 equivalents of an acid;
    ii. 0 to 5 equivalents of an organic base or an inorganic base;
    iii. optionally, a buffer solution; and
    iv. an XYTA source selected from XYTA and $M_2$XYTA (Formula III)

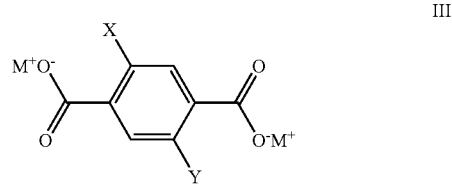

III wherein M is K or Na, and wherein the molar ratio of XYTA to the 2,3,5,6-tetraaminotoluene salt is from 1:1 to 1:1.1; thereby adjusting the pH of the mixture to between about 3 and about 10 and thereby producing and precipitating the complex generally described by Formula (I); and
  c. cooling, filtering, and washing the precipitated complex.

BRIEF DESCRIPTION OF THE DRAWINGS

The invention is illustrated by way of example and not limited by the accompanying figures.

FIG. 1 is a schematic representation of an embodiment of the process described herein.

DETAILED DESCRIPTION

The following description is exemplary and explanatory only and is not restrictive of the invention, as defined in the appended claims.

A process is provided for preparing a complex generally described by Formula I

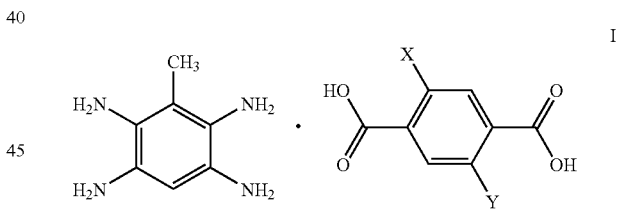

I wherein X and Y are each independently selected from the group consisting of H, OH, SH, methyl, ethyl, F, Cl, and Br; comprising the sequential steps under exclusion of oxygen:
  a. contacting 2,3,5,6-tetraaminotoluene (Formula II)

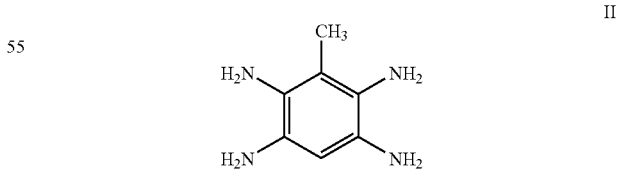

II with an aqueous solution comprising 1 to 6 equivalents of acid per mol of 2,3,5,6-tetraaminotoluene, optionally heating the solution, thereby dissolving the 2,3,5,6-tetraaminotoluene;
  b. combining the dissolved 2,3,5,6-tetraaminotoluene with
    i. 0 to 5 equivalents of an acid;
    ii. 0 to 5 equivalents of an organic base or an inorganic base;

iii. optionally, a buffer solution; and
iv. an XYTA source selected from XYTA and M₂XYTA (Formula III)

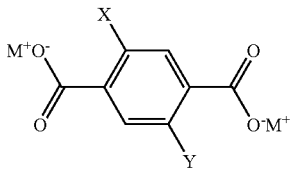

wherein M is K or Na, and wherein the molar ratio of XYTA to the 2,3,5,6-tetraaminotoluene salt is from 1:1 to 1:1.1; thereby adjusting the pH of the mixture to between about 3 and about 10 and thereby producing and precipitating the complex generally described by Formula (I); and c. cooling, filtering, and washing the precipitated complex.

In one embodiment of this process, the process further comprises preparing the 2,3,5,6-tetraaminotoluene for use in step (a) by contacting 2,6-diamino-3,5-dinitrotoluene (IV)

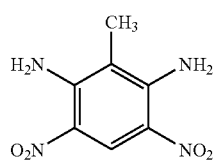

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (II); and subsequently filtering the reaction mixture, thereby removing the spent hydrogenation catalyst.

In the context of this disclosure, a number of terms shall be utilized.

As used herein, the term "TAT salt" or, equivalently, "2,3,5,6-tetraaminotoluene salt," denotes a compound formed by reaction of 2,3,5,6-tetraaminotoluene with an acid such as HCl, acetic acid, $H_2SO_4$, or $H_3PO_4$. One example of a TAT salt is TAT.4HCl.

As used herein, the term "XYTA" denotes 2-X-5-Y-terephthalic acid, where X and Y are independently selected from the group consisting of H, OH, SH, methyl, ethyl, F, Cl, and Br. One example is 2,5-dihydroxyterephthalic acid, in which X=Y=OH. The disodium or dipotassium salt of the diacid is represented by the term "M₂XYTA" where M is Na or K.

As used herein, the term "net yield" of a product denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

In the process described herein, a solution of TAT species is formed and reacts with a source of XYTA at a pH between about 3 and about 10, and thereby producing and precipitating the complex generally described by Formula (I). TAT may be prepared, for example, by hydrogenation of 2,6-diamino-3,5-dinitrotoluene in the presence of a heterogeneous catalyst.

One embodiment of the process described herein that explicitly includes the production of TAT by hydrogenation of 2,6-diamino-3,5-dinitrotoluene is illustrated in FIG. 1; possible minor modifications will be evident to one skilled in the art. The 2,6-diamino-3,5-dinitrotoluene can be made by reacting 2,6-dihalo-3,5-dinitrotoluene with ammonia as described in co-pending U.S. Provisional Application 61/138,662 which is by this reference incorporated in its entirety as a part hereof for all purposes. Suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these catalysts, Pt/C is preferred. The catalyst is typically used in the amount of about 0.5 to about 5.0 wt % metal based on 2,6-diamino-3,5-dinitrotoluene.

An aqueous suspension of 2,6-diamino-3,5-dinitrotoluene, hydrogenation catalyst 22, and water 19 is contacted with hydrogen 21 in the presence of about 0 to about 1 mol equivalent of $NH_{3(g)}$ 20 to form a reaction mixture. With reference to FIG. 1, the hydrogenation is carried out in an aqueous suspension in a reactor 18 at a temperature between about 20 and about 100° C., preferably between about 60° C. and about 85° C., and a hydrogen pressure of between about 45 and about 500 psi (0.31 to 3.45 MPa), preferably about 300 psi (2.07 MPa), in the presence of about 0 to about 1 mol equivalent of $NH_{3(g)}$ 20. Reaction continues for a time sufficient to consume about 6 to 7 mol equivalents of hydrogen, thereby producing 2,3,5,6-tetraaminotoluene ("TAT"). The time required depends on the details of the specific set up but is typically about 2 hours.

A small amount of tin (e.g., about 0.5 wt % tin powder) may be added as well at this stage to reduce any oxidized species that may be present and prevent additional oxidation.

In one embodiment, as shown in FIG. 1, about 1 to about 6 equivalents, preferably about 1 to about 3 equivalents, of an acid 23 are added to dissolve the TAT; as a result, a soluble acid salt of TAT is formed, herein referred to as "TAT salt." Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an adsorbent material capable of absorbing impurities. Examples of adsorbent materials include without limitation active carbon, alumina and microporous styrene.

The resulting reaction mixture 24 is then filtered 25, typically at a temperature in the range of about 60° C. to about 80° C., to remove the spent hydrogenation catalyst 26, preferably by passing through a carbon filter bed. The spent catalyst can then be recycled.

Because the reaction mixture may have picked up small amounts of oxygen by this point, nitrogen 36 is typically blown through it 34 in a deoxygenation step. A small amount of tin 37 (e.g., about 0.5 wt % tin powder) may be added as well to reduce oxidized species and prevent additional oxidation. The temperature at this stage is typically about 35° C. to about 40° C.

To achieve high productivity in the complex formation process, the complex (I) is directly formed from the dissolved TAT with the divalent aromatic acid salt shown generally described by Formula III ("$M_2XYTA$", where M is K or Na) in an aqueous reaction solution. X and Y are each independently selected from the group consisting of H, OH, SH, methyl, ethyl, Cl, F, and Br.

In a preferred embodiment, X and Y are each OH and M is potassium, so that the divalent aromatic acid salt is the dipotassium salt of 2,5-dihydroxyterephthalic acid (Formula V)

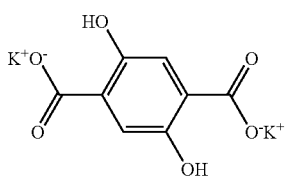

V ("$K_2DHTA$"), which may be formed by the reaction of 2,5-dihydroxyterephthalic acid with KOH; or, as described in U.S. Pat. No. 6,040,478 (col. 3, lines 47-59), by contacting hydroquinone with potassium carbonate and carbon dioxide, optionally in the form of potassium bicarbonate, with the reaction being carried out in the presence of potassium formate at a temperature above 160° C., preferably 175-225° C., so that the resulting $K_2DHTA$ product is formed in a few hours in a quantitative yield.

The complex TAT.XYTA (Formula I) is produced 38 by combining the filtered, deoxygenated reaction mixture with about 0.5 to about 5 equivalents of a source of the XYTA moiety 39 and adjusting the pH to produce and precipitate the complex. This is done under a nitrogen atmosphere 43 to exclude oxygen. The XYTA source can be the diacid XYTA, the salt $M_2XYTA$ (M=K or Na), or a mixture of XYTA and $M_2XYTA$. The pH is adjusted to between about 3 and about 10, preferably between about 5 and about 8, i.e. the pH range at which the complex is least soluble, to precipitate the desired 1:1 complex and maximize yield. The pH is adjusted to the desired value using 0 to 5 equivalents of an acid; 0 to 5 equivalents of an organic base or an inorganic base; and, optionally, a buffer solution. Water may be used as well.

Examples of suitable acids include without limitation HCl, acetic acid, $H_2SO_4$, and $H_3PO_4$. Examples of suitable organic bases include without limitation aliphatic amines (for example, triethylamine) and carboxylates like acetate (acetate might need to be used in conjunction with a stronger base). Examples of suitable inorganic bases include without limitation KOH, NaOH, alkali carbonates, alkali bicarbonates, and ammonia. The acids and/or bases should not form undesirable products irreversibly when added to the reaction mixture. Also, any salt byproducts produced during complex formation should be readily removable (e.g., soluble in the reaction mixture or extractable with a solvent that does not dissolve the complex).

In the embodiment shown in FIG. 1, streams of water 40 and a basic solution 41 (for example, 2 equivalents NaOH) are added. The temperature of the mixture is initially about 40° C. to about 100° C., typically about 50° C. to about 60° C., and is gradually cooled to a temperature between about 5° C. to about 15° C. to promote complete precipitation of the complex. The preferred precipitation temperature will depend on the product concentration and on the amount of impurities present, but is generally chosen between about 0° and about 40° C., preferably between about 0° and about 20° C.

Various designs are possible for combining the dissolved TAT with the XYTA source and whatever acid, base, and/or buffer solutions are used to adjust the pH. FIG. 1 shows one embodiment in which a stream of TAT salt in an acid solution 34, the XYTA source 39, water 40, and base 41 are fed concurrently or consecutively into a vessel 38 wherein complex formation and precipitation take place. The XYTA source 39, water 40, and base 41 are most conveniently added as a single solution. In other embodiments, TAT dissolved in an acid solution could be introduced into a vessel containing a basic XYTA source solution, or the XYTA source stream could be fed into the vessel containing the TAT dissolved in an acid solution. Alternatively, the XYTA source and TAT dissolved in an acid solution could be fed concurrently or consecutively into a buffer solution at the desired pH or into a basic solution to which an acid solution is subsequently added. Which design is best for a specific situation will be evident to one skilled in the art.

The TAT.XYTA complex is recovered from the reaction mixture by filtration at a temperature in of the range of about 5° C. to about 50° C., preferably about 10° C. to about 15° C., and washed with water 45 and methanol 47, typically at a temperature in the range of about 15° C. to about 40° C. The methanol is recycled (47, 48) and a purge is drawn to prevent accumulation. Aqueous washes are discarded. In the embodiment shown in FIG. 1, there are two purge streams for aqueous wastes (42, 46), one of which (42) contains most of the Sn used in the deoxygenation step. The washed and dried TAT.XYTA complex 50 is kept under nitrogen 49 to protect it from oxygen. It is of high enough quality and purity to produce polybenzimidazole polymer of high enough molecular weight to make high performance fibers.

The process described herein is an efficient and effective way to produce high purity TAT.XYTA complexes from 2,6-diamino-3,5-dinitrotoluene, particularly the 1:1 complex of TAT and 2,5-dihydroxyterephthalic acid, which can be used to make polybenzimidazole polymer for high performance fibers. This process design eliminates costly intermediate drying and recrystallization steps. The recycling of spent catalyst and methanol streams contributes economical and environmental advantages.

The materials, methods, and examples herein are illustrative only and, except as specifically stated, are not intended to be limiting.

EXAMPLES

This invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials 2,6-diamino-3,5-dinitrotoluene ("DADNB"), >96% pure, was as described in co-pending U.S. Provisional Application 61/138,662, which is by this reference incorporated in its entirety as a part hereof for all purposes.

2,3,5,6-tetraaminotoluene tetrahydrochloride was prepared as described in co-pending U.S. Provisional Application 61/138,602, which is by this reference incorporated in its entirety as a part hereof for all purposes.

2,3,5,6-tetraaminotoluene was prepared as follows. 2,3,5, 6-tetraaminotoluene tetrahydrochloride (55 g, 0.194 mol)

was dissolved in 150 mL of deaerated water, heated to 80° C. for 30 minutes and combined with sodium hydroxide pellets (6.47 g, 0.162 mol). To this suspension was added a 100 mL aqueous solution of sodium hydroxide (32.28 g, 0.81 mol) and the mixture was allowed to cool to room temperature. The precipitated TAT free base was filtered off, washed with water (4×15 mL) and dried under vacuum.

K$_2$DHTA (dipotassium salt of 2,5-dihydroxyterephthalic acid) was made according to the method described in U.S. Pat. No. 6,040,478 (col. 3, lines 47-59). Its purity was between 98 and 99.8% with the major impurity potassium formate. The K$_2$DHTA was dried to constant weight at 70° C. under vacuum to remove water.

Dry basis 5% Pt on C ("5% Pt/C"), wetted with 50% water, Degussa F101, was obtained from Degussa, now Evonik Degussa, a subsidiary of Evonik Industries AG, Essen, Germany.

The meaning of abbreviations is as follows: "equiv" means equivalent(s), "g" means gram(s), "$^1$H NMR" means proton nuclear magnetic resonance spectroscopy, "h" means hour(s), "L" means liter(s), "mg" means milligram(s) "mL" means milliliter(s), "mmol" means millimole(s), "mol" means mole(s), "MPa" means megapascals, "ppm" means parts per million, "psi" means pounds per square inch, and "UV" means ultraviolet spectroscopy.

Example 1

This example demonstrates the preparation of TAT.4HCl from 2,6-diamino-3,5-dinitrotoluene.

A 1 L stirred Hastelloy autoclave was charged with 119 g of crude DADNT wet cake (about 0.49 mol), and 2.4 g of 5% Pt/C catalyst. The autoclave was purged 5 times with N$_2$ and 2 times with H$_2$ at 90 psi (0.62 MPa). Subsequently, 600 mL of deaerated water (purged with N$_2$ overnight) was added and the mixture was pressurized at 81° C. to 300 psi (2.07 MPa). Hydrogenation was continued for a total time of 3 h with an approximate uptake of 6.5 mol equivalents of H$_2$. The excess hydrogen was released and the autoclave was cooled to 40° C. and purged twice with N$_2$, after which 240 g of deaerated HCl$_{aq}$ (34%, by titration) was added. The mixture was stirred and heated back up to 80° C., then passed through a carbon bed filter at 75° C. to remove catalyst and a small amount of unconverted starting material. A total of about 1.0 L of a red-orange colored reaction solution was collected containing an equivalent of approximately 134 g of TAT.4HCl. (0.45 mol).

Example 2

This example demonstrates the preparation of TAT.DHTA from the TAT.4HCl solution prepared as in Example 1.

12.47 g of K$_2$DHTA (45.52 mmol) along with 5.82 g of sodium hydroxide (145.45 mmol) was added to a reaction vessel. This was followed by the addition of 180 mL of deaerated water and heating to 75° C. About 100 g aqueous TAT.4HCl salt solution made as described in Example 1 (equivalent to net 12.43 g of 2,5-diamino-3,5-dinitrotoluene) and 100 mg of tin powder (0.91 mmol) were heated to 75° C. to effect complete dissolution. The TAT salt solution was subsequently pumped into the basic K$_2$DHTA solution over a period of 5 minutes, which resulted in precipitation of a yellow solid. This mixture was then cooled to 25° C. with stirring for 1.5 hours. The mixture was subsequently filtered and washed with water (50 mL) and methanol (50 mL). The solid light yellow product was allowed to dry for 18 hours under a stream of nitrogen at 40° C.

The net yield was 12.8 g (80%). $^1$H-NMR analysis indicated product purity >99% with a TAT:DHTA ratio of 1.00: 1.01. The material was analyzed by UV for oxidative decomposition products 3,6-diimino-2-methylcyclohexa-1,4-diene-1,4-diamine (Formula VI), 1,9-dimethylphenazine-2,3,7,8-tetraamine (Formula VII) and 1,6-dimethylphenazine-2,3,7,8-tetraamine) (Formula VIII). No VII or VIII and less than 100 ppm of VI were detected.

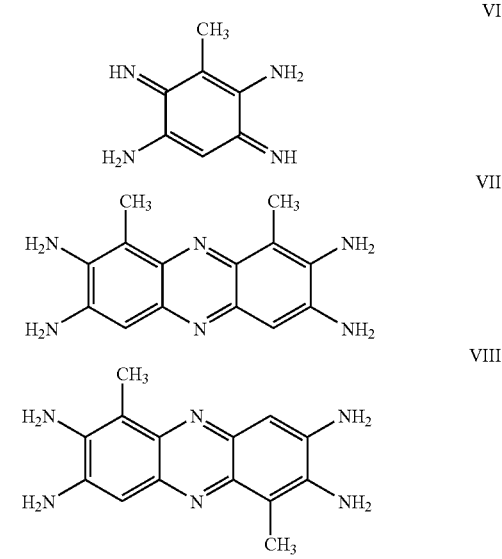

Example 3

This example demonstrates a larger-scale preparation of a high-purity complex of 2,3,5,6-tetraaminotoluene with 2,5-dihydroxyterephthalic acid dipotassium salt in the presence of Sn powder as a reducing agent.

TAT.4HCl (144.47 g, 0.485 mol, 1.1 equiv) was added to a 2 L bottle along with tin powder (0.78 g, 0.0066 mol, 0.015 equiv) and purged with nitrogen to ensure an inert atmosphere. To this vessel was added deaerated water (810 g). The solution was heated to 75° C. In a separate 1 L vessel, K$_2$DHTA (120.88 g, 0.441 mol, 1 equiv) and NaOH (37.0 g, 0.925 mol, 2.1 equiv) were combined, purged thoroughly with nitrogen, dissolved in water (810 g) and heated to 50° C. The TAT.4HCl solution was added to the K$_2$DHTA/NaOH solution over 35 minutes which resulted in the formation of a flocculant light yellow precipitate. This mixture was then cooled to 25° C. over 90 minutes while being stirred. The light yellow solid was recovered by filtration, washed with water (80 mL) and methanol (80 mL), and was dried over two days under vacuum. This provided 147 g (95% net yield) of a light yellow solid. NMR analysis indicated a 1.00:1.00 ratio of TAT to DHTA.

Example 4

This example demonstrates the preparation from polymer from a TAT.DHTA complex prepared according to the process described herein.

The TAT.DHTA complex produced is Example 3 was polymerized using the following conditions: Total Mass: 15 g; TAT.DHTA complex (1.9 g); Solids: 10%; Tin powder: 9 mg; Polyphosphoric acid: 12.1 g and P$_2$O$_5$: 0.9 g. The mixture was mixed using an overhead mechanical stirrer and was subjected to the following temperature profile: 1 hour at 100° C.; 16 hours at 120° C. and 9 hours at 180° C. This gave a polymer with IV of 36.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. A process for preparing a complex generally described by Formula I

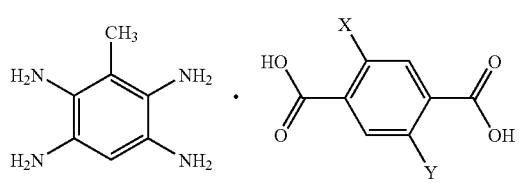

wherein X and Y are each independently selected from the group consisting of H, OH, SH, methyl, ethyl, F, Cl, and Br; comprising the sequential steps under exclusion of oxygen:

a. contacting 2,3,5,6-tetraaminotoluene (Formula II)

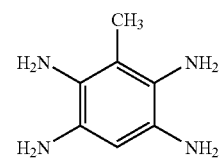

with an aqueous solution comprising 1 to 6 equivalents of acid per mol of 2,3,5,6-tetraaminotoluene, optionally heating the solution, thereby dissolving the 2,3,5,6-tetraaminotoluene;
b. combining the dissolved 2,3,5,6-tetraaminotoluene with
   i. 0 to 5 equivalents of an acid;
   ii. 0 to 5 equivalents of an organic base or an inorganic base;
   iii. optionally, a buffer solution; and
   iv. an XYTA source selected from XYTA and $M_2$XYTA (Formula III)

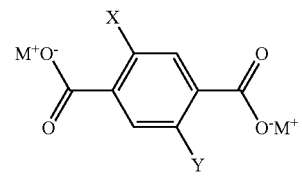

wherein M is K or Na, and wherein the molar ratio of XYTA to the 2,3,5,6-tetraaminotoluene salt is from 1:1 to 1:1.1; thereby adjusting the pH of the mixture to between about 3 and about 10 and thereby producing and precipitating the complex generally described by Formula (I); and
c. cooling, filtering, and washing the precipitated complex.

2. The process of claim 1 further comprising preparing the 2,3,5,6-tetraaminotoluene for use in step (a) by contacting 2,6-diamino-3,5-dinitrotoluene (IV)

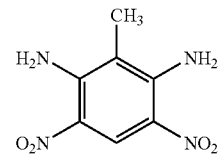

with a hydrogenation catalyst and hydrogen gas, in water in a reaction vessel, to form a reaction mixture, at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene (II); and subsequently filtering the reaction mixture, thereby removing the spent hydrogenation catalyst.

3. The process of claim 1 wherein the acid is selected from the group consisting of HCl, acetic acid, $H_2SO_4$, and $H_3PO_4$.

4. The process of claim 1 where the aqueous solution of step (a) further comprises a co-solvent selected from the group consisting of methanol, ethanol, and isopropanol.

5. The process of claim 1 wherein step (b) is carried out at a temperature between about 10° and about 100° C.

6. The process of claim 1 wherein X and Y are each OH, the acid in steps (a) and (b) is HCl, and M is K.

* * * * *